United States Patent
Takagi et al.

(10) Patent No.: US 9,488,741 B2
(45) Date of Patent: Nov. 8, 2016

(54) X-RAY ENERGY SPECTRUM MEASUREMENT METHOD, X-RAY ENERGY SPECTRUM MEASUREMENT APPARATUS, AND X-RAY CT APPARATUS

(71) Applicant: Hitachi, Ltd., Tokyo (JP)

(72) Inventors: Hiroyuki Takagi, Tokyo (JP); Isao Murata, Suita (JP)

(73) Assignee: Hitachi, Ltd., Tokyo (JP)

( * ) Notice: Subject to any disclaimer, the term of this patent is extended or adjusted under 35 U.S.C. 154(b) by 22 days.

(21) Appl. No.: 14/687,948

(22) Filed: Apr. 16, 2015

(65) Prior Publication Data

US 2015/0301202 A1 Oct. 22, 2015

(30) Foreign Application Priority Data

Apr. 18, 2014 (JP) ................... 2014-086712

(51) Int. Cl.
| | | |
|---|---|---|
| *G01T 1/36* | (2006.01) | |
| *A61B 6/03* | (2006.01) | |
| *A61B 6/00* | (2006.01) | |
| *G01N 23/04* | (2006.01) | |

(52) U.S. Cl.
CPC ............ *G01T 1/36* (2013.01); *A61B 6/032* (2013.01); *A61B 6/482* (2013.01); *A61B 6/583* (2013.01); *G01N 23/046* (2013.01)

(58) Field of Classification Search
USPC ........................................ 378/18, 16, 54, 89
See application file for complete search history.

(56) References Cited

U.S. PATENT DOCUMENTS 4,323,779 A * 4/1982 Albert .................... A61B 6/145
378/113

FOREIGN PATENT DOCUMENTS

JP 2007-524438 A 8/2007

OTHER PUBLICATIONS

Akira Iwasaki et al., Characteristic Features of a High-Energy X-Ray Spectra Estimation Method Based on the Waggener Iterative Perturbation Principle, Japanese Society for Therapeutic Radiology and Oncology, 2005, pp. 79-95, vol. 17, No. 2.
Weggener-Iwasak, Hirosaki University Repository for Academic Resources, 2008.

* cited by examiner

*Primary Examiner* — Kiet T Nguyen
(74) *Attorney, Agent, or Firm* — Mattingly & Malur, PC

(57) ABSTRACT

Provided is an X-ray energy spectrum estimation method capable of reproducing, with high precision, information on an attenuation path to which an X-ray is irradiated, and performing, with high precision, reconstruction of an X-ray CT image by enabling high-precision estimation of spectrum of energy released from an X-ray source device. An energy spectrum estimation device (92) normalizes a response function, and calculates a modified efficiency matrix from the normalized response function, a detection efficiency matrix, and a measurement-system correction coefficient. The energy spectrum estimation device then calculates a particular result in accordance with a Bayesian estimation equation, without divergence, with use of the calculated modified efficiency matrix, the normalized modified efficiency matrix, and an attenuation characteristic curve obtained by a measurement circuit (30). The energy spectrum (92) calculates an X-ray energy spectrum by dividing, by the normalized modified efficiency matrix, the particular result obtained by the Bayesian estimation equation.

10 Claims, 6 Drawing Sheets

ATTENUATION CHARACTERISTIC CURVE yA($t_i$) OBTAINED AT EACH ANGULAR POSITION BY MEASURING X-RAY AFTER PATH TROUGH THE ATTENUATION PLATE OF THICKNESS $t_i$

X-RAY ENERGY SPECTRUM MEASUREMENT METHOD, X-RAY ENERGY SPECTRUM MEASUREMENT APPARATUS, AND X-RAY CT APPARATUS

BACKGROUND OF THE INVENTION

1. Field of the Invention

The present invention relates to a method of and apparatus for measuring an energy spectrum of an X-ray consisting of polychromatic photons, and to an X-ray CT apparatus using an X-ray consisting of polychromatic photons.

2. Description of Related Art

There is known an X-ray spectrum estimation method according to which a specimen is irradiated with an X-ray to reconstruct a CT image, for example, as described in an article titled "Characteristic Features of A High-Energy X-Ray Spectrum Estimation Method Based on The Waggener Iterative Perturbation Principle" by Akira Iwasaki et al., The Official Journal of the Japanese Society for Therapeutic Radiology and Oncology, Vol. 17, No. 2, pp. 79-95, 2005.

Further, JP-T-2007-524438 describes a technique for photographing a calibration phantom which is an attenuation material, together with a specimen, by irradiating them with X-rays. The resulting photographing-information is then used for calibrating light-absorption characteristics of the subject.

However, the X-ray energy spectrum estimation method (measurement method) according to the related art only measures a quantity of X-ray passed through the attenuation material. In accordance with the attenuation amount in the measured X-ray, the method estimates rough average energy of the X-ray.

Large magnitude pulse-like or direct current X-rays are irradiated in X-ray generators put to industrially and medically practical uses. Thus, many photons are simultaneously incident on a detector. Consequently, it is substantially impossible to make a simple measurement of wave height distribution for each photon.

Further, the related art method has drawbacks that accuracy of estimation results is poor, and that the estimation results have little scientific basis. Therefore, the related art method is not a practically usable technique.

In addition, in a related art X-ray CT apparatus, spectrum of energy released from an X-ray source device are unknown, and reproduction of attenuation path information necessary for reconstructing a CT image is inaccurate. Thus, the obtained CT image that has been reconstructed becomes to have its contrast representation deviating from actual density information.

Here, it is conceivable to use a Bayesian estimation equation for estimating spectrum of energy released from an X-ray source device.

However, if the Bayesian estimation equation is merely applied to the estimation of the spectrum of energy released from the X-ray source device, the estimation equation is diverged. Thus, it is difficult to obtain a desired result. Consequently, the Bayesian estimation equation cannot appropriately be applied.

An object of the present invention is to provide an X-ray energy spectrum measurement method, an X-ray energy spectrum measurement apparatus, and an X-ray CT apparatus, in which spectrum of energy released from an X-ray source device are estimated with high precision, thereby information on a path length with respect to an X-ray irradiation can be obtained precisely, and an X-ray CT image can be reconstructed with high precision.

SUMMARY OF THE INVENTION

To attain the above object, the present invention is configured as follows.

(1) An X-ray energy spectrum measurement method according to the present invention includes: causing an X-ray generated from an X-ray source to pass through an attenuation material whose thickness changes stepwise or continuously; moving the attenuation material for changing the thickness of the attenuation material through which the X-ray generated from the X-ray source passes; detecting the X-ray passed through the attenuation material; calculating an attenuation characteristic curve of the detected X-ray; calculating an X-ray energy spectrum, from the attenuation characteristic curve of the X-ray, in accordance with a Bayesian estimation equation with use of at least a normalized response function and modified efficiency matrix.

(2) An X-ray energy spectrum measurement apparatus according to the present invention includes: an X-ray source which generates an X-ray; an attenuation material through which the X-ray generated from the X-ray source passes, the attenuation material changing in thickness stepwise or continuously; a movement mechanism which moves the attenuation material for changing a thickness of the attenuation material through which the X-ray generated from the X-ray source passes; a detector which detects the X-ray passed through the attenuation material; and an X-ray energy computation unit.

The X-ray energy computation unit calculates an attenuation characteristic curve of the X-ray detected by the detector. Further, the X-ray energy computation unit estimates an X-ray energy spectrum of the X-ray generated by the X-ray source, from the attenuation characteristic curve of the X-ray, in accordance with a Bayesian estimation equation with use of at least a normalized response function and a modified efficiency matrix.

(3) An X-ray CT apparatus according to the present invention includes: an X-ray source which generates an X-ray; an attenuation material through which the X-ray generated from the X-ray source passes the attenuation material changing in thickness stepwise or continuously; a movement mechanism which moves the attenuation material for changing the thickness of the attenuation material through which the X-ray generated from the X-ray source passes; a detector which detects the X-ray passed through the attenuation material; an X-ray energy computation unit; a memory which stores an energy spectrum of the X-ray generated by the X-ray source, the energy spectrum being computed by the X-ray energy computation unit; a correction computation processing unit which reconstructs an image of a specimen; and an output unit which displays the image of the specimen that has been reconstructed by the correction computation processing unit.

The above X-ray energy computation unit calculates an attenuation characteristic curve of an X-ray detected by the detector. Further, the X-ray energy computation unit estimates an X-ray energy spectrum of the X-ray generated by the X-ray source, from the attenuation characteristic curve of the X-ray, in accordance with a Bayesian estimation equation with use of at least a response function normalized and a modified efficiency matrix.

The present invention can provide an X-ray energy spectrum measurement method, an X-ray energy spectrum measurement apparatus, and an X-ray CT apparatus, each capable of reproducing, with high precision, information on an attenuation path to which an X-ray is irradiated, and performing, with high precision, reconstruction of an X-ray CT image by enabling high-precision estimation of energy spectrum emitted from an X-ray source device.

DESCRIPTION OF THE PREFERRED EMBODIMENTS

Hereinafter, embodiments of the present invention are described with reference to the drawings.

First Embodiment

Figure 1:
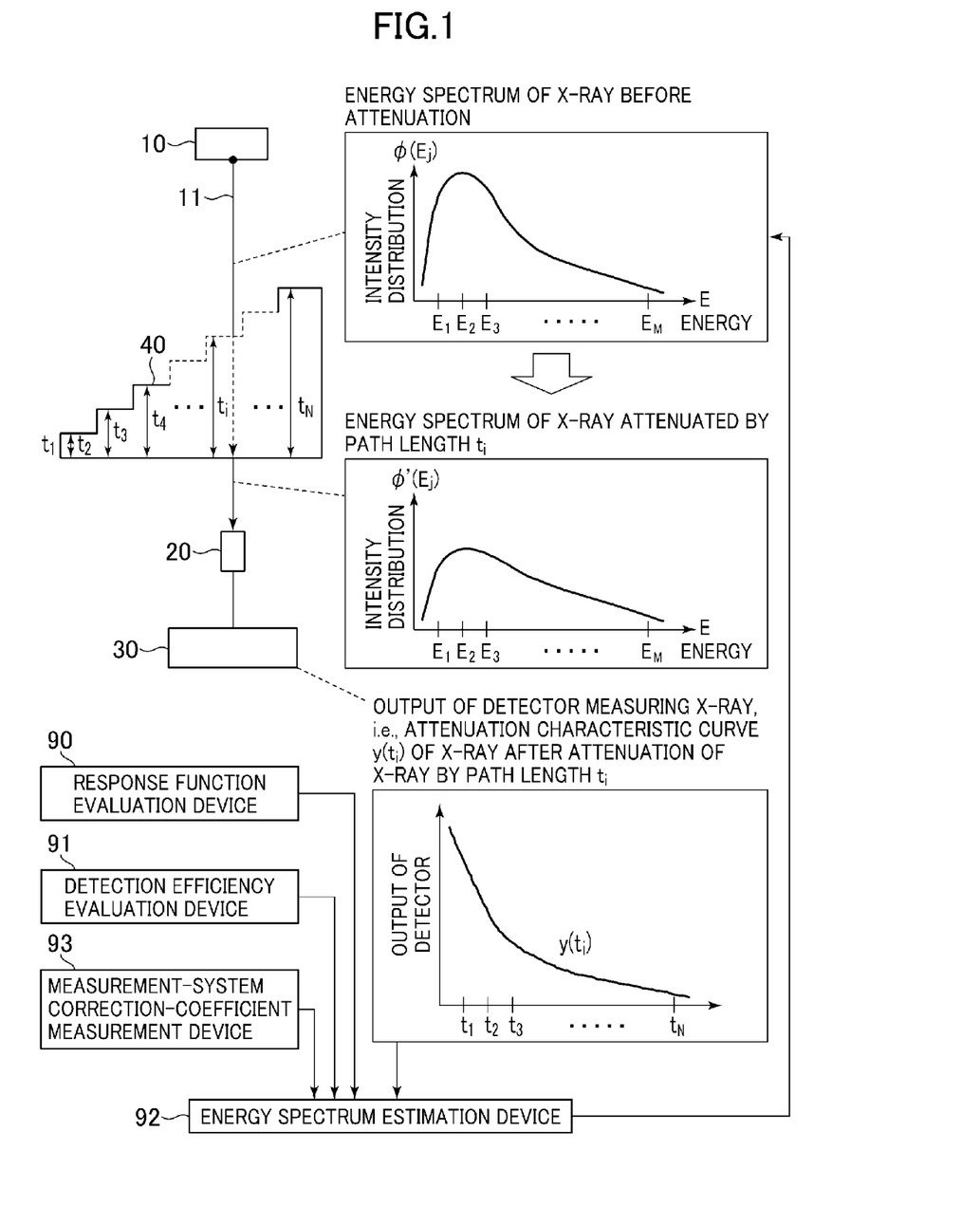
FIG. 1 is a diagram illustrating an operation of an X-ray energy spectrum measurement apparatus according to a first embodiment of the present invention.
Figure 2:
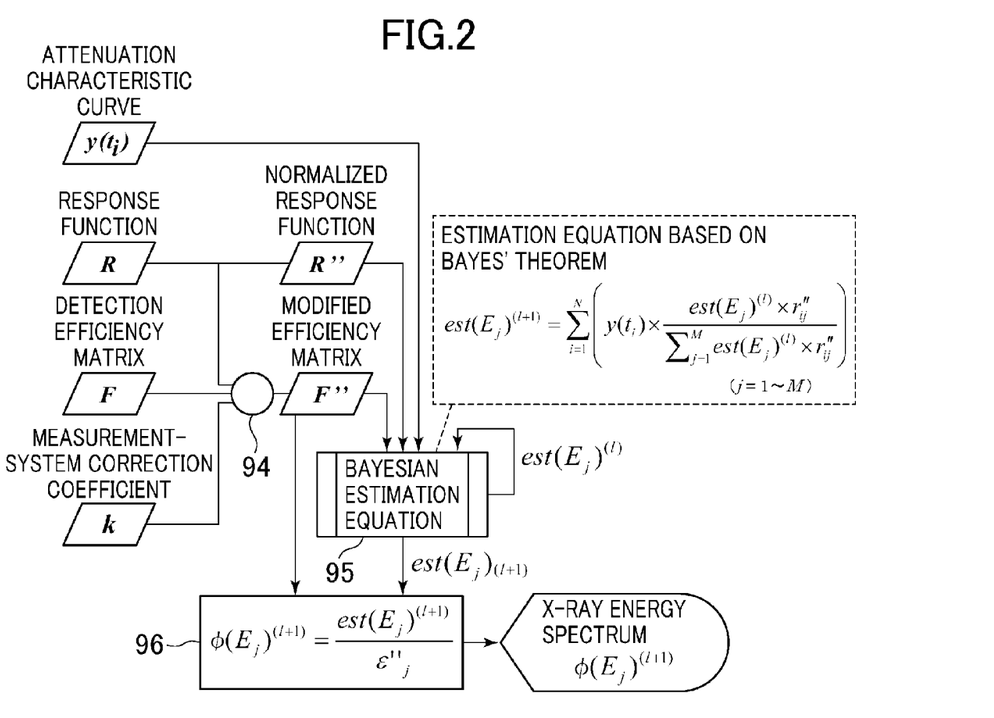
FIG. 2 is a diagram illustrating a detailed data flow of and computation equations used by the X-ray energy spectrum measurement apparatus according to the first embodiment of the present invention.
Figure 3:
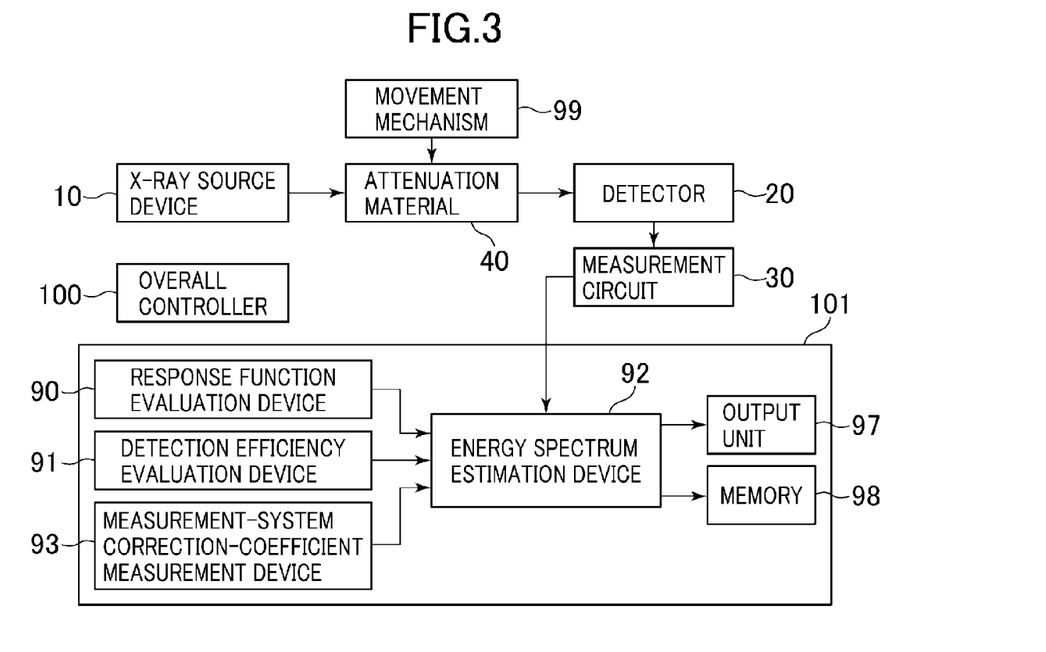
FIG. 3 is a block diagram schematically illustrating a configuration of the first embodiment of the present invention.

FIGS. 1 and 2 are diagrams each illustrating an operation of an X-ray energy spectrum measurement apparatus according to a first embodiment of the present invention. FIG. 3 is a block diagram schematically illustrating a configuration of the first embodiment of the present invention.

First, the configuration according to the first embodiment of the present invention is described with reference to FIG. 3.

In FIG. 3, the X-ray energy spectrum measurement apparatus which is the first embodiment of the present invention includes an X-ray source device (X-ray source) 10, a movement mechanism 99 moving an attenuation material 40, a detector 20 detecting an X-ray passed through the attenuation material 40, and a measurement circuit 30 to which a detection signal is supplied from the detector 20.

Further, the above X-ray energy spectrum measurement apparatus includes an energy spectrum estimation device 92 to which a measurement signal from the measurement circuit 30 is supplied, a response function evaluation device 90 supplying a response function to the energy spectrum estimation device 92, a detection efficiency evaluation device 91 supplying a detection efficiency to the energy spectrum estimation device 92, a measurement-system correction-coefficient measurement device 93 supplying a measurement-system correction coefficient to the energy spectrum estimation device 92, an output unit 97 displaying an estimated energy spectrum output from the energy spectrum estimation device 92, and a memory 98 storing the estimated energy spectrum output from the energy spectrum estimation device 92.

The energy spectrum estimation device 92, the response function evaluation device 90, the detection efficiency evaluation device 91, the measurement-system correction-coefficient measurement device 93, the output unit 97, and the memory 98 configure an X-ray energy computation unit 101.

Further, an operation of each unit, device, and equipment illustrated in FIG. 3 is controlled by an overall control unit 100.

In FIG. 1, the detector 20 is disposed to face the X-ray source device 10 emitting an X-ray beam 11 that has an X-ray energy spectrum $\Phi(E_j)$ (j=1 to M). Further, the attenuation material 40 changing a transmission thickness of X-ray from $t_1$ to $t_N$ stepwise is disposed between the X-ray source device 10 and the detector 20.

Incidentally, the minimum thickness of the attenuation material 40 may be 0. That is, the attenuation material 40 may be an airspace. In addition, the attenuation material 40 may be a material which changes the transmission thickness continuously.

An X-ray passed through the attenuation material 40 is incident on the detector 20. A signal output of the detector 20 is amplified by the measurement circuit 30. Then, the amplified signal is digitally converted. Thus, a detector-output $y(t_i)$ is obtained by measuring the X-ray attenuated at a transmission thickness $t_i$ (i=1 to N).

In the first embodiment, the attenuation material 40 is moved by the movement mechanism 99. Consequently, an attenuation thickness, at which the X-ray to be incident on the detector 20 is attenuated in the attenuation material 40, can be changed stepwise. That is, the attenuation thickness can be increased to $t_N$ from $t_1$ at which the attenuation material 40 is an airspace, through the second smallest transmission thickness $t_2$, and the third smallest transmission thickness $t_3$. Accordingly, an attenuation characteristic curve $y(t_i)$ (i=1 to N) of the X-ray can be measured.

For the attenuation material 40, any composition can be employed, either a single element or a mixture, as long as a linear attenuation coefficient $\mu_j$ (j=1 to M) associated with each of energy-levels $E_1, E_2, \ldots E_M$ on the X-ray spectrum in question is obtained.

The X-ray before attenuation has the energy spectrum as shown in FIG. 1. By passing through the attenuation material having a transmission thickness $t_N$, the X-ray changes its intensities at each energy levels to $\Phi'(E_1)=\Phi(E_1)\cdot\exp(-\mu_1\cdot t_N)$, $\Phi'(E_2)=\Phi(E_1)\cdot\exp(-\mu_2\cdot t_N), \ldots \Phi'(E_M)=\Phi(E_M)\cdot\exp(-\mu_M\cdot t_N)$.

That is, a process of attenuation of the X-ray energy spectrum $\Phi(E_j)$ (j=1 to M) at the corresponding one of the transmission thicknesses $t_1, t_2, \ldots t_N$ can be represented by a response function R employing, as composing-elements of N-rows and M-columns, attenuation coefficients $r_{ij}$ each corresponding to a set of the energy-level $E_j$ and the transmission thickness $t_i$.

Incidentally, the response function R can be calculated by the response function evaluation device 90 performing computer-simulation based on physical and chemical data.

On the other hand, generally, a detection efficiency in detecting an X-ray being incident on the detector 20 takes values varying with energy-levels. Thus, the detection efficiency at each energy-level $E_j$ can be represented by $\epsilon_j$ (j=1 to M). At that time, the detection efficiency can be represented as a detection efficiency matrix F having M-rows and N-columns. In addition, each matrix component of the matrix F can be defined as $f_{ij}=\delta_{ij}\times\epsilon_j$ using a Dirac delta function.

Generally, the efficient matrix is expressed in a unit which is, e.g., a quantity [Q] of electric charge output when one photon having a certain energy-level $E_j$ is incident on the detector 20, i.e., [Q/Photon]. Incidentally, the detection efficiency $\epsilon_j$ can be calculated by the detection efficiency evaluation device 91 that has a configuration obtained by simulating the configuration of an actual detector and that performs a simulation calculation.

Furthermore, in order to reproduce a measurement of an actual X-ray, a measurement-system correction coefficient k for correcting a measurement circumstance, such as a geometry of an actual measurement system and an efficiency required to convert the quantity of electric charge into a voltage, is needed, in addition to the response function R and the detection efficiency matrix F. However, in a case where it is unnecessary to calculate an absolute value of the number of photons, and where only an energy distribution has to be calculated, the measurement-system correction coefficient k may have an arbitrary value.

By use of each of the above functions, the energy spectrum estimation device 92 measures, with the configuration illustrated in FIG. 1, the attenuation characteristic curve $y(t_i)$ as following equation (1).

$$y(t_i)=k\cdot R\cdot F\cdot \Phi(E_j) \quad (1)$$

However, in order to apply an analytical technique based on a Bayes' theorem relating to conditional probability, a computation is performed as expressed in the following equation (2) using a response function R" normalized so that a column-wise sum of the matrix R is 1.

$$k\cdot R\cdot F=R''\cdot F'' \quad (2)$$

At that time, a modified efficiency matrix F" is an m×m square matrix whose matrix components $f''_{ij}$ are given by the following equation (3).

$$f''_{ij}=\delta_{ij}\times\epsilon''_j \quad (3)$$

Thus, the component $\epsilon''_j$ is given by the following equation (4).

$$\epsilon''_j=k\cdot\epsilon_j\cdot\Sigma r_{ij} \ (i=1 \text{ to } N) \quad (4)$$

FIG. 2 is a diagram illustrating a detailed data flow and computation equations.

In FIG. 2, the response function evaluation device 90 can output a response function R and a normalized response function R". The normalized response function R" output from the response function evaluation device 90 is supplied to a Bayesian equation computation unit 95. Further, the response function R and the normalized response function R" output from the response function evaluation device 90, the detection efficiency matrix F output from the detection efficiency evaluation device 91, and the measurement-system correction coefficient k output from the measurement-system correction-coefficient measurement device 93 are supplied to a computing-unit 94. Then, the computing-unit 94 computes a modified efficiency matrix F" from the response function R, the normalized response function R", the detection efficiency matrix F, and the measurement-system correction-coefficient k. The modified efficiency matrix F" computed by the computing-unit 94 is supplied to the Bayesian equation computation unit 95. Further, the attenuation characteristic curve output from the measurement circuit 30 is also afforded to the Bayesian equation computation unit 95.

The Bayesian equation computation unit 95 uses the attenuation characteristic curve $y(t_i)$, the normalized response function R", and the modified efficiency matrix F" to compute the following estimation equation based on the Bayes' theorem, and obtains an energy spectrum $est(E_j)^{(l+1)}$.

$$est(E_j)^{(l+1)} = \sum_{i=1}^{N}\left(y(t_i)\times \frac{est(E_j)^{(l)}\times r''_{ij}}{\sum_{j=1}^{M} est(E_j)^{(l)}\times r''_{ij}}\right) \quad \text{[Expression 1]}$$

$$(j = 1 \sim M)$$

The energy spectrum $est(E_j)^{(l+1)}$ computed by the Bayesian estimation equation computation unit 95 is supplied to a dividing-unit 96.

The modified efficiency matrix F" is also supplied to the dividing-unit 96. The dividing-unit 96 normalizes the detection efficiency $\epsilon_j$ among the components of the modified efficiency matrix F" to calculate $\epsilon''_j$. Then, the dividing-unit 96 divides $est(E_j)^{(l+1)}$ by $\epsilon''_j$. Thus, the X-ray energy spectrum $\Phi(E_j)^{(l+1)}$ of the X-ray generated by the X-ray source 10 is calculated.

$$\phi(E_j)^{(l+1)} = \frac{est(E_j)^{(l+1)}}{\epsilon''_j} \quad \text{[Expression 2]}$$

Then, the calculated X-ray energy spectrum is displayed in the output unit 97.

Incidentally, the computing-unit 94, the Bayesian estimation equation computation unit 95, and the dividing-unit 96 are provided in the energy spectrum estimation device 92.

That is, estimation based on the Bayes' theorem is applied iteratively. Then, a result of the estimation is divided by $\epsilon''_j$. Consequently, the X-ray energy spectrum $\Phi(E_j)$ (j=1 to M) of the X-ray originally released by the X-ray source 10 can be calculated.

Further, if the value of k is evaluated with high accuracy, the absolute value of the number of photons existing at each energy-level of the X-ray energy spectrum can be evaluated with very high precision by the measurement-system correction-coefficient measurement device 93 that uses a standard gamma-ray source in which the number of photons and photon energy emitted per unit time are known.

As described above, the first embodiment of the present invention is configured as follows. That is, the response function is normalized. Then, the modified efficiency matrix is calculated from the normalized response function, the detection efficiency matrix, and the measurement-system correction coefficient. A particular result is calculated in accordance with the Bayesian estimation equation with use of the calculated modified efficiency matrix, the normalized response function, and the attenuation characteristic curve obtained by the measurement circuit 30. Consequently, an estimation result can be obtained without divergence. Then, the particular result obtained by the above Bayesian estimation equation is divided by the normalized modified efficiency matrix. Thus, the X-ray energy spectrum can be calculated with high precision.

Accordingly, accurate X-ray energy spectrum can be calculated highly accurately.

Second Embodiment

Next, a second embodiment of the present invention is described with reference to FIG. 4.

In the present embodiment, an X-ray source device 10 is used, which emits, in a direction corresponding to an X-ray emission angle, a fan-beam X-ray 50 having an X-ray energy spectrum $\Phi A(E_j)$ (j=1 to M). A line-sensor-type detector array 21 consisting of a plurality of detectors arranged like a line is disposed in an irradiation area of X-rays to face the X-ray source device 10. Further, an attenuation material 41 that covers the entire fan-beam area and that can change the transmission thickness of the attenuation material 41 from $t_1$ to $t_N$ stepwise is disposed between the X-ray source device 10 and the detector array 21.

According to the second embodiment of the present invention, the attenuation material 41 having a stepwise stacked shape moves in a direction vertical to a fan-beam plane of the X-ray source device 10. Thus, the attenuation thickness of X-rays being incident on all of the detectors configuring the detector array 21 can efficiently be changed stepwise.

Next, an attenuated X-ray is incident on one element in the detector 21. An output signal of the element is amplified by a multichannel measurement circuit 31. Then, the amplified signal is digitally converted. Thus, an attenuation characteristic curve $yA(t_i)$ can be obtained at each of the positions of all of the detectors, that is, at a position corresponding to each X-ray emission angle.

Figure 4:
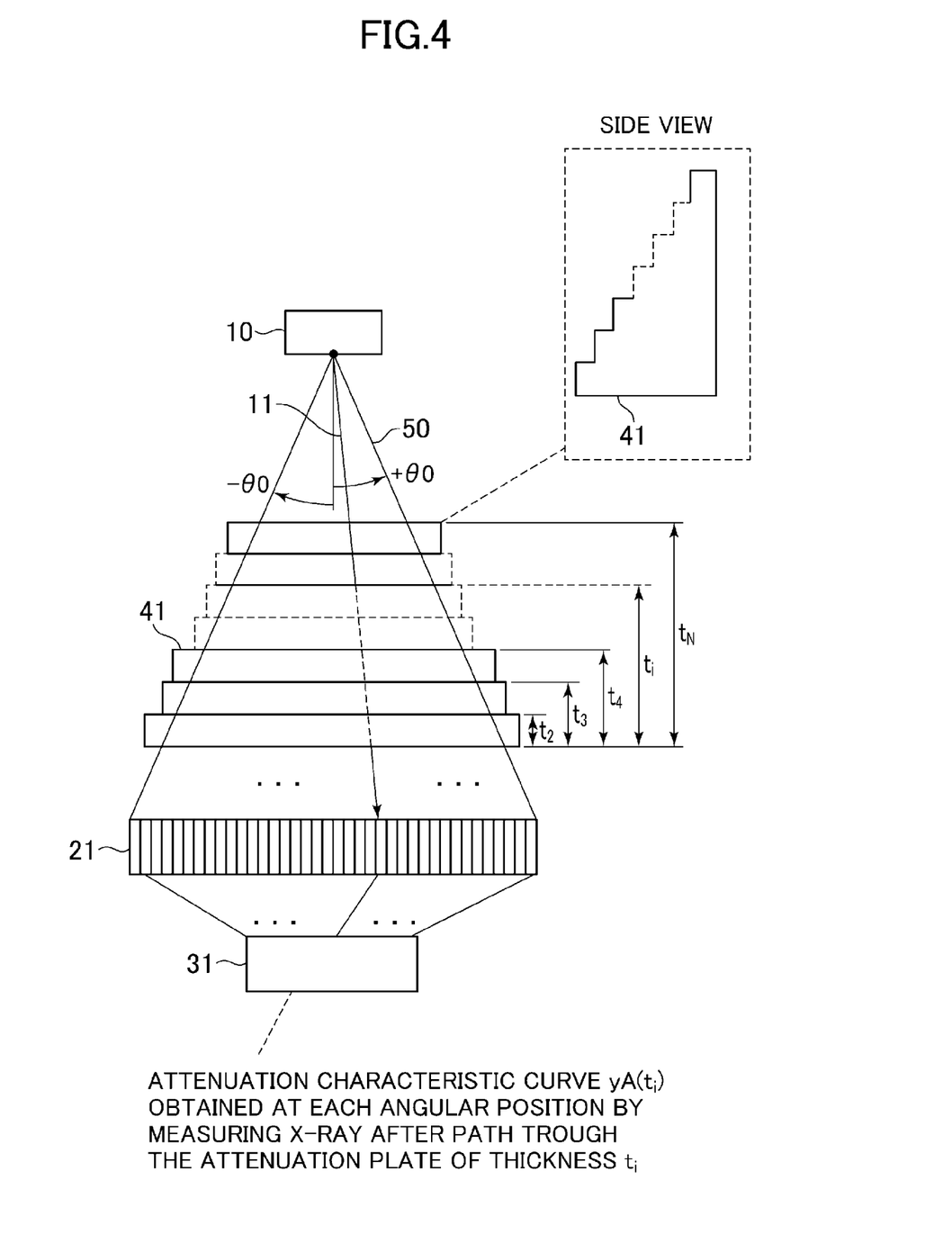
FIG. 4 is a diagram illustrating an operation of an X-ray energy spectrum measurement apparatus according to a second embodiment of the present invention.

The attenuation characteristic curves $yA(t_i)$ obtained by the multichannel measurement circuit 31 are omitted in FIG. 4. However, the attenuation characteristic curves $yA(t_i)$ are supplied to an X-ray energy computation unit configured similarly to the X-ray energy computation unit 101 illustrated in FIG. 3. Thus, an X-ray energy spectrum, which is obtained before the attenuation, is calculated. The calculated X-ray energy spectrum is displayed in a display unit, and stored in a memory.

Incidentally, the second embodiment is also provided with an overall control unit 100, similarly to the first embodiment.

Similarly to the above first embodiment, the second embodiment can measure an X-ray energy spectrum at each channel, i.e., at each X-ray emission angle within the X-ray fan-beam 50 by performing, on each channel, estimation according to the Bayes' theorem.

This means that an angular distribution of the X-ray energy spectrum is measured at each X-ray emission angle.

Figure 5:
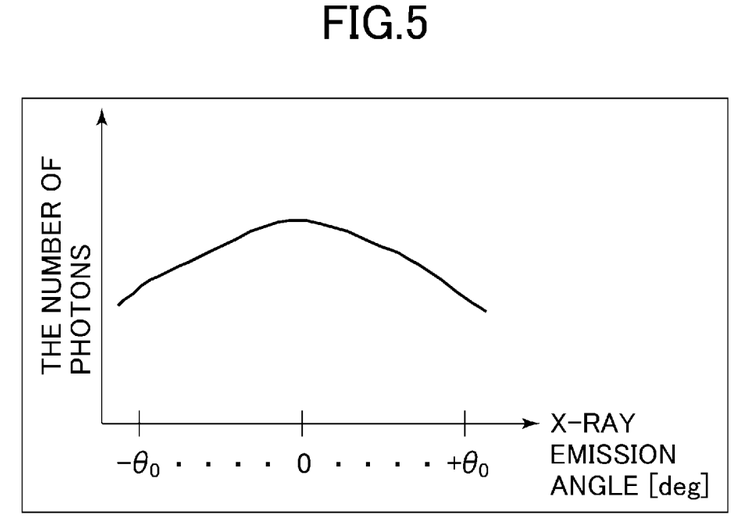
FIG. 5 is a graph illustrating the number of photons versus an X-ray emission angle according to the second embodiment of the present invention.
Figure 6:
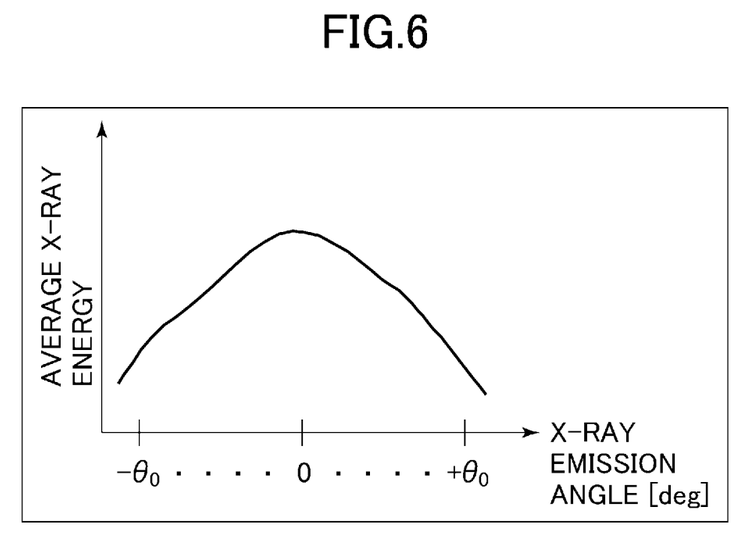
FIG. 6 is a graph illustrating average X-ray energy versus the X-ray emission angle according to the second embodiment of the present invention.

FIGS. 5 and 6 are graphs each illustrating an example of a result of measurement of the angular distribution according to the second embodiment of the present invention.

FIG. 5 is a graph illustrating the number of photons versus the X-ray emission angle. FIG. 6 is a graph illustrating average X-ray energy versus the X-ray emission angle.

As illustrated in FIGS. 5 and 6, the distribution of the number of photons in the fan-beam area, and the distribution of the average energy in the fan-beam area can be displayed in the output unit 97. According to these data, a reaction process of X-rays being incident on the detector array 21 can be evaluated highly accurately.

The second embodiment of the present invention can calculate, with high precision, accurate X-ray energy spectrum at each X-ray emission angle of the X-ray source 10.

Third Embodiment

Figure 7:
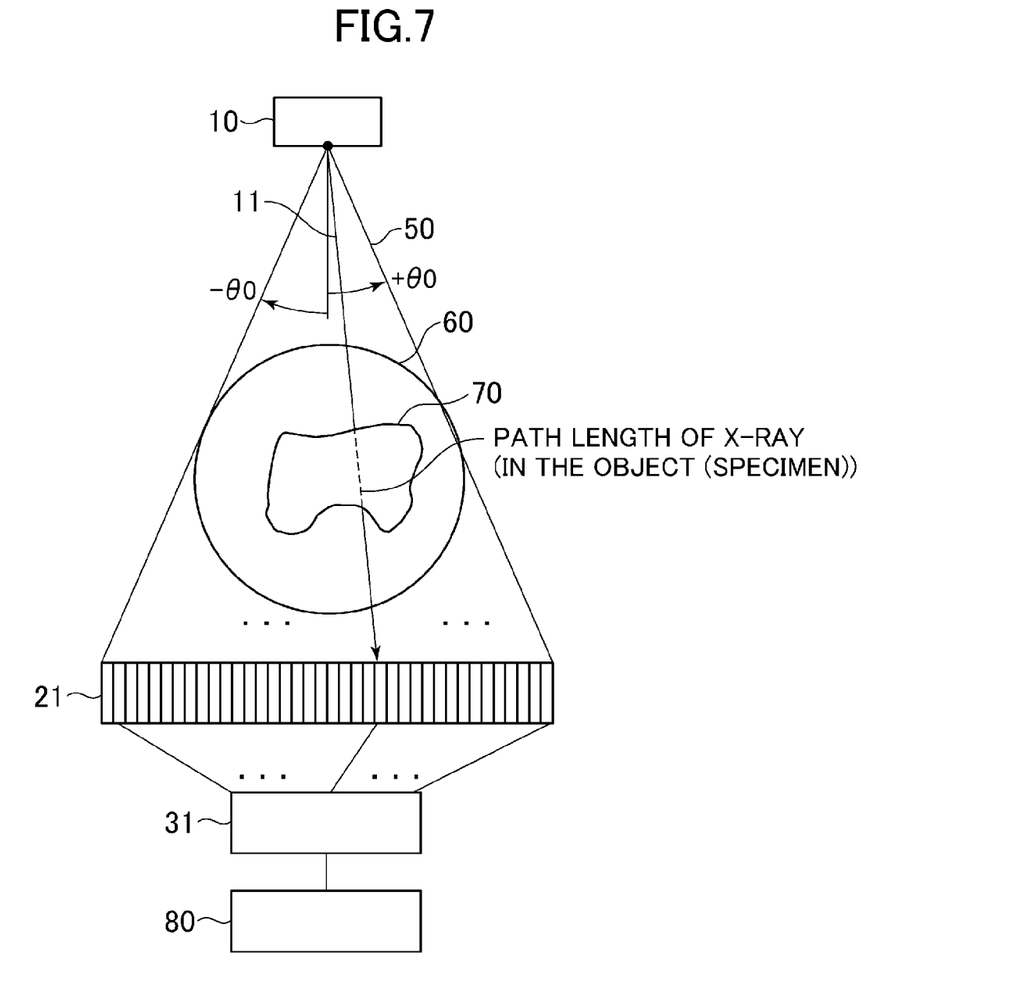
FIG. 7 is a diagram illustrating an operation of an X-ray energy spectrum measurement apparatus according to a third embodiment of the present invention.

Next, a third embodiment of the present invention is described with reference to FIG. 7.

In the present embodiment, a specimen 70 is mounted on a scanner table 60 of an actual X-ray CT apparatus. An intensity signal representing the intensity of an X-ray passed through the specimen 70 is measured by a multichannel measurement circuit 31. Then, a reconstruction computation is performed on obtained projection data in an image reconstruction device 80.

Like the second embodiment of the present invention, X-ray energy spectrum and the angular distribution thereof are preliminarily measured using an attenuation material 41. The measured X-ray energy spectrum and the angular distribution thereof are stored in the image reconstruction device 80. A correction computation using X-ray energy spectrum data corresponding to each channel is performed in an image reconstruction computation process. Consequently, attenuation path information can be reproduced with good accuracy. Accordingly, a quality, such as a density resolution, of a CT image can be enhanced.

Figure 8:
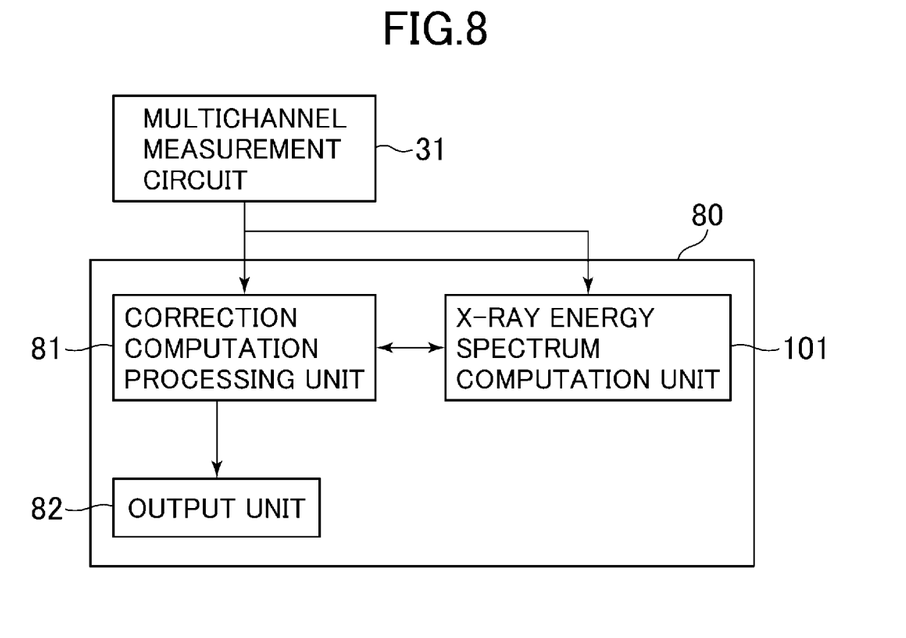
FIG. 8 is a diagram illustrating an internal configuration of an image reconstruction device according to the third embodiment of the present invention.

FIG. 8 is a diagram illustrating an internal configuration of the image reconstruction device 80. In FIG. 8, the image reconstruction device 80 includes a correction computation processing unit 81, an X-ray energy computation unit 101 equivalent to that illustrated in FIG. 3, and an output unit 82.

The X-ray energy computation unit 101 computes an X-ray energy spectrum, in accordance with an attenuation characteristic curve of the attenuation material 41 output from the multichannel measurement circuit 31, similarly to the first embodiment. Then, the X-ray energy computation unit 101 causes a memory 98 to store the computed X-ray energy spectrum corresponding to each X-ray emission angle.

The correction computation processing unit 81 compares X-ray energy spectrum data of an X-ray passed through the specimen 70, detected by a detector 21, and supplied from the multichannel measurement circuit 31 with the X-ray energy spectrum corresponding to each X-ray emission angle, which is stored in the memory 98 of the X-ray energy computation unit 101. The correction computation processing unit 81 corrects attenuation path information of the specimen 70 and reconstructs a specimen image. Then, the reconstructed image of the specimen 70 is supplied to the output unit 82 and displayed therein.

According to the third embodiment of the present invention, X-ray energy spectrum actually applied especially to industrial and medical uses can be grasped with good accuracy. The performance evaluation and the quality assurance of photographing-results, and the quality of CT images can be improved.

As described above, according to the present invention, a high-precision novel X-ray energy spectrum measurement method having a scientific basis can be provided to a really applied large radiation dose of X-rays.

Further, the present invention provides an X-ray CT apparatus capable of appropriately correcting a phenomenon caused due to the bias of energy components included in an X-ray, that is, a phenomenon in which a proportional relation between contrast in a CT image and a material density is extremely impaired, using information concerning results of scientifically-grounded high-precision novel X-ray energy spectrum measurements performed on a really applied large radiation dose of X-rays, and also capable of identifying, with good accuracy, an actually contained material from a CT image.

In terms of quality of X-rays there has been a problem with X-rays applied especially to industrial and medical uses. According to an X-ray energy spectrum measurement method of the present invention, however, energy spectrum of X-rays which are relevant to the quality of X-rays can be measured with good accuracy by a scientifically proper method. Thus, the present invention has an advantage in enabling the quality assurance of X-ray beams utilized in industrial and medical field sites.

Further, the X-ray CT apparatus according to the present invention has advantages in dramatically solving a conventional problem that the reproduction of attenuation path information required to reconstruct a CT image is inaccurate because the spectrum of energy released from the X-ray source device is unknown, and in enabling enhancement of accuracy of a CT image. Especially, the X-ray CT apparatus according to the present invention has an enormous advantage in suppressing an abnormal CT contrast value due to a phenomenon that, in a material whose atomic number is large, attenuation of a low energy component of an X-ray consisting of non-monochromatic photons is not proportionate to the atomic number.

In addition, according to the X-ray CT apparatus of the present invention, a beneficial effect in terms of preventive maintenance, such as foreseeing of hidden deterioration of an X-ray source device can be obtained by periodically measuring X-ray energy spectrum and tracing temporal change of the X-ray energy spectrum.

What is claimed is:

1. An X-ray energy spectrum measurement method comprising:
    causing an X-ray generated from an X-ray source to pass through an attenuation material whose thickness changes stepwise or continuously;
    moving the attenuation material by use of a movement mechanism for changing the thickness of the attenuation material through which the X-ray generated from the X-ray source passes;
    detecting the X-ray passed through the attenuation material;
    calculating an attenuation characteristic curve of the detected X-ray; calculating an X-ray energy spectrum, from the attenuation characteristic curve of the X-ray, in accordance with a Bayesian estimation equation with use of at least a normalized response function and modified efficiency matrix; normalizing the modified efficiency matrix; dividing the calculated X-ray energy spectrum by the normalized modified efficiency matrix; and thereby estimating the X-ray energy spectrum of the X-ray generated by the X-ray source.

2. An X-ray energy spectrum measurement method according to claim 1, wherein the modified efficiency matrix is calculated by use of the response function, the normalized response function, a detection efficiency matrix, and a measurement-system correction coefficient.

3. An X-ray energy spectrum measurement method according to claim 2, wherein:
    the X-ray source generates a fan-beam X-ray; and
    the X-ray passed through the moving attenuation material is detected by a detector in which a plurality of detectors are arranged in a line.

4. An X-ray energy spectrum measurement apparatus comprising:
    an X-ray source which generates an X-ray;
    an attenuation material through which the X-ray generated from the X-ray source passes, the attenuation material changing in thickness stepwise or continuously;
    a movement mechanism which moves the attenuation material for changing the thickness of the attenuation material through which the X-ray generated from the X-ray source passes;
    a detector which detects the X-ray passed through the attenuation material; and
    an X-ray energy computation unit configured to calculate an attenuation characteristic curve of the X-ray detected by the detector, and
    estimate an X-ray energy spectrum of the X-ray generated by the X-ray source, from the attenuation characteristic curve of the X-ray, in accordance with a Bayesian estimation equation with use of at least a normalized response function and a modified efficiency matrix.

5. An X-ray energy spectrum measurement apparatus according to claim 4, wherein the X-ray energy computation unit includes:
    a response function evaluation unit which outputs a response function and a normalized response function;
    a detection efficiency evaluation unit which outputs a detection efficiency evaluation matrix;
    a measurement-system correction-coefficient measurement unit which outputs a measurement-system correction coefficient;
    an energy spectrum estimation unit which estimates an X-ray energy spectrum of the X-ray generated by the X-ray source, from the attenuation characteristic curve of the X-ray, in accordance with the Bayesian estimation equation with use of the response function, the normalized response function, the detection efficiency matrix, and the measurement-system correction coefficient; and
    an output unit which displays the X-ray energy spectrum estimated by the energy spectrum estimation unit.

6. An X-ray energy spectrum measurement apparatus according to claim 5, wherein the energy spectrum estimation unit includes:
    a Bayesian estimation equation computation unit which calculates an energy spectrum, from the attenuation characteristic curve of the X-ray, in accordance with the Bayesian estimation equation;
    a computing-unit which computes a modified efficiency matrix from the response function, the normalized response function, the detection efficiency matrix, and the measurement-system correction coefficient; and
    a dividing-unit configured to
    normalize the modified efficiency matrix,
    divide, the energy spectrum calculated in accordance with the Bayesian estimation computation unit, by the normalized modified efficiency matrix, and
    calculate an X-ray energy spectrum of the X-ray generated by the X-ray source.

7. An X-ray energy spectrum measurement apparatus according to claim 5, wherein:
    the X-ray source generates a fan-beam X-ray; and
    the detector includes a plurality of detectors arranged in a line.

8. An X-ray CT apparatus comprising:
    an X-ray source which generates an X-ray;

an attenuation material through which the X-ray generated from the X-ray source passes, the attenuation material changing in thickness stepwise or continuously;

a movement mechanism which moves the attenuation material for changing a thickness of the attenuation material through which the X-ray generated from the X-ray source passes;

a detector which detects the X-ray passed through the attenuation material;

an X-ray energy computation unit configured to calculate an attenuation characteristic curve of an X-ray detected by the detector, and estimate an X-ray energy spectrum of the X-ray generated by the X-ray source, from the attenuation characteristic curve of the X-ray, in accordance with a Bayesian estimation equation with use of at least a response function normalized and a modified efficiency matrix;

a memory which stores an energy spectrum of the X-ray generated from the X-ray source, the energy spectrum being computed by the X-ray energy computation unit;

a correction computation processing unit configured to compare data of the X-ray obtained by the detector, the X-ray having passed through a specimen, with the X-ray energy spectrum stored in the memory, correct attenuation path information of the specimen, and reconstruct an image of the specimen; and an output unit which displays the specimen image reconstructed by the correction computation processing unit.

9. An X-ray CT apparatus according to claim 8, wherein the X-ray energy computation unit includes:

a response function evaluation unit which outputs a response function and a normalized response function;

a detection efficiency evaluation unit which outputs a detection efficiency evaluation matrix;

a measurement-system correction-coefficient measurement unit which outputs a measurement-system correction coefficient;

an energy spectrum estimation unit which estimates an X-ray energy spectrum of the X-ray generated by the X-ray source, from the attenuation characteristic curve of the X-ray, in accordance with the Bayesian estimation equation with use of the response function, the normalized response function, the detection efficiency matrix, and the measurement-system correction coefficient; and an output unit which displays the X-ray energy spectrum estimated by the energy spectrum estimation unit.

10. An X-ray CT apparatus according to claim 9, wherein the energy spectrum estimation unit includes:

a Bayesian estimation equation computation unit which calculates an energy spectrum, from the attenuation characteristic curve of the X-ray, in accordance with the Bayesian estimation equation;

a computing-unit which computes a modified efficiency matrix from the response function, the normalized response function, the detection efficiency matrix, and the measurement correction coefficient; and a dividing-unit configured to normalize the modified efficiency matrix, divide, the energy spectrum calculated in accordance with the Bayesian estimation computation unit, by the normalized modified efficiency matrix, and calculate an X-ray energy spectrum of the X-ray generated by the X-ray source.

* * * * *